(12) United States Patent
Shen et al.

(10) Patent No.: US 10,520,493 B2
(45) Date of Patent: Dec. 31, 2019

(54) METHOD FOR ASSESSMENT OF NEURAL FUNCTION BY ESTABLISHING ANALYSIS MODULE

(71) Applicants: NATIONAL CHENG KUNG UNIVERSITY, Tainan (TW); NATIONAL CHENG KUNG UNIVERSITY HOSPITAL, Tainan (TW)

(72) Inventors: Meng-Ru Shen, Tainan (TW); Lian-Yun Chang, Tainan (TW); Yuan-Ting Sun, Tainan (TW); Jang-Yang Chang, Tainan (TW)

(73) Assignees: NATIONAL CHENG KUNG UNIVERSITY, Tainan (TW); NATIONAL CHENG KUNG UNIVERSITY HOSPITAL, Tainan (TW)

( * ) Notice: Subject to any disclaimer, the term of this patent is extended or adjusted under 35 U.S.C. 154(b) by 0 days.

(21) Appl. No.: 14/657,128

(22) Filed: Mar. 13, 2015

(65) Prior Publication Data
US 2016/0266101 A1  Sep. 15, 2016

(51) Int. Cl.
*G01N 33/50* (2006.01)
*G01N 33/58* (2006.01)

(52) U.S. Cl.
CPC ....... *G01N 33/5058* (2013.01); *G01N 33/582* (2013.01)

(58) Field of Classification Search
CPC .................... G01N 33/5058; G01N 33/582
USPC ........................................................ 435/325
See application file for complete search history.

(56) References Cited

U.S. PATENT DOCUMENTS 5,981,165 A * 11/1999 Weiss ..................... C07K 14/47
                                                       424/93.7
8,809,302 B2 * 8/2014 Cohen ................... A61K 31/137
                                                       514/171

OTHER PUBLICATIONS

Malchiodi-Albedi et al., CNF1 Improves Astrocytic Ability to Support Neuronal Growth and Differentiation in vitro, PLoS ONE, vol. 7, Iss. 4, Apr. 2012, e34115, pp. 1-12.*

Schmitz et al., Automated analysis of neuronal morphology, synapse number and synaptic recruitment, Journal of Neuroscience Methods, 195 (2011) pp. 185-193.*
Hong et al., Monitoring Neurite Morphology and Synapse Formation in Primary Neurons for Neurotoxicity Assessments and Drug Screening, Thermo Scientific, 2012, Available online at: www.thermofisher.com/content/dam/LifeTech/global/life-sciences/Cell%20analysis/pdf/ NeurotoxicityAssessment.pdf.*
Shin et al., Expression of mutant huntingtin in glial cells contributes to neuronal excitotoxicity, JCB, vol. 171, No. 6, (2005), pp. 1001-1012.*
Thomas J.F. Nieland, et al., High Content Image Analysis Identifies Novel Regulators of Synaptogenesis in a High-Throughput RNAi Screen of Primary Neurons, PLOS ONE, Mar. 2014, pp. 1-11, vol. 9, Issue 3, e91744.
Tseng-Jung Liu, et al., Effect of Age on Nuclear Size in Parasympathetic Postganglionic Neurons, Journal of Meiho University, No. 10, (Apr. 1992), published Mar. 4, 2011, 2 pages.
Yue Huang, et al., A Computational Framework for Studying Neuron Morphology From In Vitro High Content Neuron-based Screening, Journal of Neuroscience Methods, Jul. 15, 2010, vol. 190, Issue 2, pp. 299-309.
Enrique R. Torre, et al., Demonstration of Local Protein Synthesis within Dendrites using a New Cell Culture System that Permits the Isolation of Living Axons and Dendrites from Their Cell Bodies, The Journal of Neuroscience, Mar. 1992, 12(3), pp. 762-772.

* cited by examiner

*Primary Examiner* — Jennifer M. H. Tichy
(74) *Attorney, Agent, or Firm* — Birch, Stewart, Kolasch & Birch, LLP (57) ABSTRACT

A method for assessment of neural function by establishing an analysis module is revealed. The first step of the method is to capture images of the cultured cells with a plurality of fluorescence labeling by a fluorescence microscopy system for image analysis. The cultured cells include neurons and non-neuronal cells. Then select neurons with neurites having fluorescence labeling and exclude non-neuronal cells according to an area and a fluorescence intensity of nucleus. Also calculate an area of the neuronal cell body, a length of the neurites and a number of processes and branches to verify outgrowth of the neurites of the neurons. Next calculate a number of synaptic puncta having fluorescence labeling on the area of the neurites having fluorescence labeling defined in Step 2 to verify formation of the synaptic puncta of the neurons for assessment of neural function.

7 Claims, 9 Drawing Sheets
(2 of 9 Drawing Sheet(s) Filed in Color)

FIG. 9 ly to a method by which neurite outgrowth and function are analyzed fast and representatively. The method uses important markers related to neurite outgrowth in combination with optimized image analysis flow and program commands. Thereby the method can not only assess nerve growth and formation of neural network at early stage but also act as a high-content drug screening platform for quickly detecting the effect of drugs on neural function.

Descriptions of Related Art

With the progress of cancer therapies, survival rate of cancer patients is increased markedly. Recently, due to the extension of life span of cancer patients, side effects of chemotherapy drugs have drawn much more attention. Among the side effects of chemotherapy, neuropathy significantly affects patient's quality of life. Hence, the development of appropriate pre-clinical assay models and objective assessments of chemotherapy-associated neurotoxicity are thus the critical steps to test potential therapies for toxic reduction or prevention.

The high-content analysis (HCA) has been broadly applied in immunological, cardiovascular or neurological researches. The HCA together with high-throughput screening allows users to obtain fluorescence images of cells in a multi-well plate automatically. Thus researchers can efficiently conduct tests and acquire a variety of quantitative information. However, there are some problems while using molecular markers for assessing neuronal function in high-throughput screening. Most people choose one single marker or only one single parameter to indicate neuronal function. For example, Huang Y et al. used Neuronal Class III β-Tubulin in a high content neuron-based screening for assessing morphology of neurons (J Neurosci Methods. 2010 Jul. 15; 190(2):299-309). Harrill J A et al. applied a high-content analysis to assess neurite outgrowth of primarily rat cortical neurons. The microtubule-associated protein 2 (MAP2) labeled area (dendrites) is deducted from the βIII tubulin labeled area, and the rest area represents axons (Neurotoxicology. 2013 January; 34:61-73). Nieland T J et al. used MAP2, Psd95-Syn1, and Gphn-Syn1 to define synaptogenesis (PLoS One. 2014 Mar. 14; 9(3):e91744). The methods mentioned above assess neural function only by a single indicator, such as neurite outgrowth or synaptogenesis, which is not comprehensive. However, simultaneous multiparametric analysis for detecting neurite outgrowth and synaptogenesis requires more complicate, time-consuming processes and molecular markers.

Moreover, usage of cell model for drug screening also affects analyzing procedure and duration. For example, immortalized neuronal cell lines are easier to amplify and grown but suffered from several concerns. First, chemicals added for inducing differentiation may complicate the assessment of tested drug regarding to the unpredictable drug-drug interaction. In contrast, primarily cultured cells are differentiated naturally. Second, the primarily cultured neurons shared more characteristic with normal neurons in vivo. However, primarily cultured neurons are more difficult to obtain and maintain, to optimize the in vitro culture period is essential.

To avoid aforementioned weaknesses, the high-content screening strategies combined with appropriate cell model and the automated image acquisition and analyses are essential for the establishment of efficiency and sensitivity in vitro neurotoxic assays.

SUMMARY OF THE INVENTION

A primary object of the present invention is to provide a method for assessment of neural function by establishing an analysis module, by which neurite outgrowth and function can be analyzed quickly and representatively. The method uses important markers for nerve growth together with optimized image analysis flow and program. Moreover, the method can also be used as a drug screening platform for quick detection of drug's neurotoxicity or protective effect on neurons.

In order to achieve the above objects, a method for assessment of neural function by establishing an analysis module according to the present invention includes a plurality of steps. The first step is to capture images of a cultured cell with a plurality of fluorescence labeling (including Hoechst dye for nuclei) by a fluorescence microscopy system for image analysis, wherein the cultured cells includes neurons, and a plurality of fluorescence labeling includes a fluorescence labeling of neurites and a fluorescence labeling of synaptic puncta. The second step is to select the neurons with the neurites having fluorescence labeling and exclude non-neuronal cells according to an area and a fluorescence intensity of the nucleus. Then calculate an area of neuronal cell body, a length of the neurites, and a number of processes and branches to verify outgrowth of the neurites of the neurons. The fluorescence labelings of the neurites includes microtubule-associated protein 2 (MAP2) or neuronal class III β-tubulin (TUJ1) protein while the fluorescence labeling of the synaptic puncta is synaptophysin protein or PSD95. The third step is to calculate a number of the synaptic puncta having the fluorescence labeling on the area of the neurites having fluorescence labeling defined in the second step to verify the formation of the synaptic puncta of neuron for assessment of neural function.

The cultured cells are prepared by the following steps: Step 1: obtaining a cerebral cortex from a neonatal mouse or rat (0~1 day old), adding a first medium (such as DMEM/F12 medium without serum), and triturating the cerebral cortex to get a mixture. Step 2: filtering the mixture and getting a solution with cell pellet after centrifugation. Step 3: culturing the cell pellet in a second medium for 9-12 days (10 days preferred) so as to prepare the cultured cells. The second medium contains Neurobasal® A medium, B-27® Supplement, 0.5 mM L-glutamine, and 0.5% penicillin streptomycin.

BRIEF DESCRIPTION OF THE DRAWINGS

The patent or application file contains at least one drawing executed in color. Copies of this patent or patent application publication with color drawings will be provided by the Office upon request and payment of the necessary fee.

DETAILED DESCRIPTION OF THE PREFERRED EMBODIMENT

Figure 1:
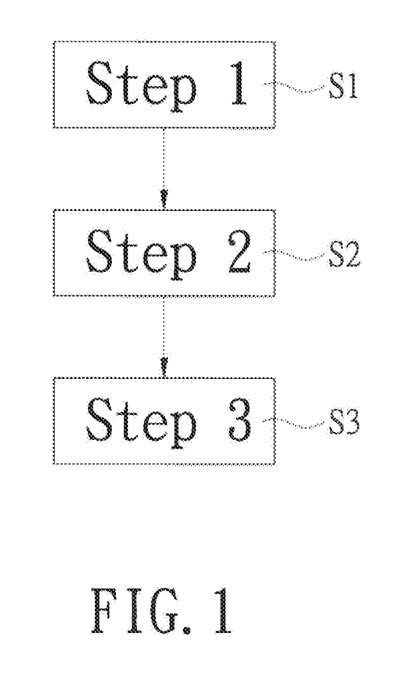
FIG. 1 is a flow chart showing steps of a method for assessment of neural function by establishing an analysis module according to the present invention.

Refer to FIG. 1, a method for assessment of neural function by establishing an analysis module according to the present invention includes the following steps:

Step 1 (S1): capturing images of a cultured cell with a plurality of fluorescence labeling (including Hoechst dye for nuclei) by a fluorescence microscopy system for performing an image analysis, wherein the cultured cells includes neurons, and the plurality of fluorescence labeling includes a fluorescence labeling of neurites and a fluorescence labeling of synaptic puncta.

Step 2 (S2): selecting neurons with neurites having fluorescence labeling and excluding non-neuronal cells according to an area and a fluorescence intensity of the nucleus, and calculating an area of neuronal cell body, a length of the neurites, and a number of processes and branches to verify outgrowth of the neurites of the neurons. The fluorescence labeling of the neurites includes microtubule-associated protein 2 (MAP2) or neuronal class III β-tubulin (TUJ1) protein while the fluorescence labeling of the synaptic puncta is synaptophysin protein or post synaptic density 95 (PSD95).

Figure 2:
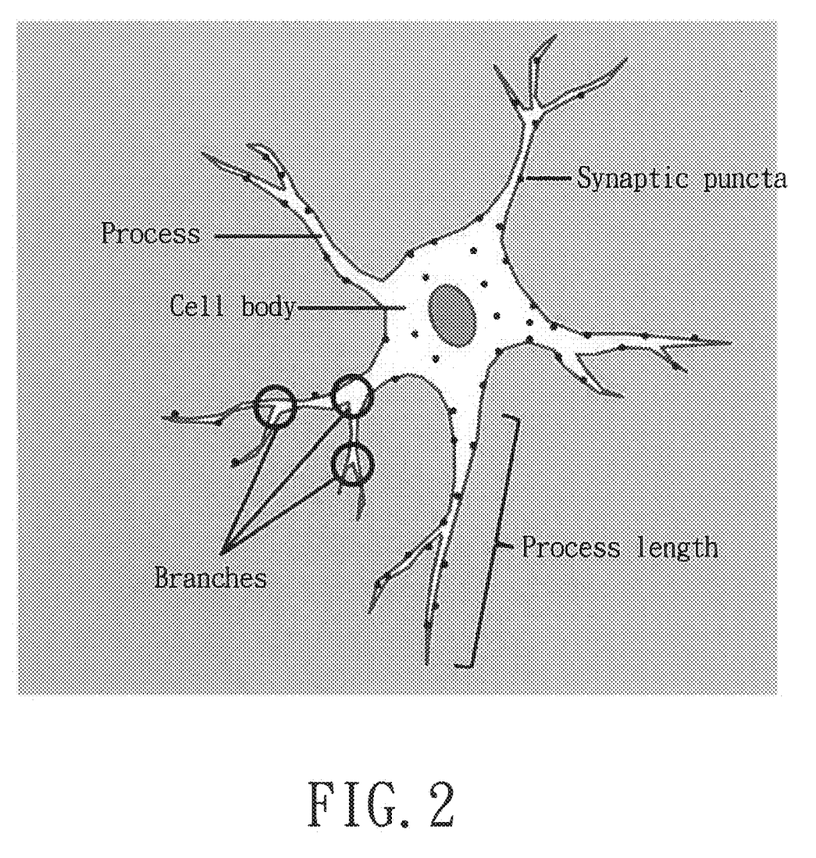
FIG. 2 is a schematic drawing showing a neuron according to the present invention.

Step 3 (S3): calculating a number of the synaptic puncta having the fluorescence labeling according to the area of the neurites labeled with fluorescence in the step 2 so as to verify formation of the synaptic puncta of the neurons for assessment of neural function. As shown in FIG. 2, a schematic drawing of a neuron is revealed.

The cultured cells mentioned in the step 1 can be prepared by methods including, but not limited to, the following. Step 1: obtaining a cerebral cortex from a neonatal mouse or rat (0~1 day old), adding a first medium (such as DMEM/F12 medium without serum), and triturating the tissue to get a mixture. Step 2: filtering the mixture and getting a solution with a cell pellet after centrifugation. Step 3: culturing the cell pellet in a second medium for 9-12 days (10 days preferred) so as to get the cultured cells. The second medium contains Neurobasal® A medium, B-27® Supplement, 0.5 mM L-glutamine, and 0.5% penicillin streptomycin.

Embodiment One

Preparing Primarily Cultured Cells and Performing Immunofluorescence Staining

Comparing with conventional method of inducing differentiation by treating cell lines with chemicals, the method uses primarily cultured cells for differentiating naturally, which shares more characteristic with normal neuron in vivo and is a better method in assessment of early formation of neural network. Moreover, the test results are not affected by drug-drug interaction. Thus the present invention uses primarily cultured cells for evaluating neural function.

(1) Preparation of Primarily Cultured Cells

Cerebral cortex was obtained from 0~1 day old B6 mice pup and meninges were removed. DMEM/F12 medium without serum was used to triturate the cortex tissue. Then, the DMEM/F12 medium without serum was refilled to 5 mL, mixed evenly with 0.5 mL trypsin, and placed at 37° C. for 5 minutes. Then the mixture with 1 mL fetal bovine serum (FBS) was filtered through a cell strainer. After a centrifugation at 3,000 rpm for 10 min, the supernatant was removed and precipitated cells were added to a medium required for nerve cell culture. The medium was prepared by adding B-27® Supplement, 0.5 mM L-glutamine, and 0.5% penicillin streptomycin to Neurobasal® A medium (2) Black multi-well microplates with clear bottom were used for nerve cell culture. Each well was coated with 70 μL poly-D-lysine or poly-L-lysine. Cells were seeded in a density of $2.8 \times 10^4$/well and cultured for 7, 10, 13, and 21 days. Then cells were fixed with 4% polyformaldehyde for 10 min and washed with PBS twice for 5 min each. Then, each well was added with 1 M glycine reacting for 10 min and wash with PBS twice for 5 min each. After cells were added with 0.05% Triton X-100 reacting for 20 min and washed with PBS twice for 5 min each, cell were blocked with 4% bovine serum albumin (BSA) for 1 hour and then stained with primary antibodies including anti-MAP2 antibody (MyBioSource; MBS502140) and anti-synaptophysin antibody (Abcam; ab32127) for 12-16 hours. Next, cell were washed twice with PBST (10 min each) and incubated with fluorescence-conjugated secondary antibodies including Alexa Fluor 488 (Jackson ImmunoResearch; 7 03-546-155) and Alexa Fluor 647 (molecular probes; A31573) and Hoechst 33258 for 1 hour. At last, cells were washed twice with PBST (10 min each) and added with PBS for further image acquisition and analysis.

Embodiment Two

Image Acquisition and Analysis

Fluorescence microscopy system was used to capture images at the wavelength of DAPI (4'-6-Diamidino-2-phenylindole), FITC (fluorescein isothiocyanate) and Cy5 for image analysis of the cultured cells mentioned above. The images were saved automatically for analysis.

To analyze neural function accurately, MetaXpress 3.1 software ("MetaXpress® Image Acquisition and Analysis Software (Analysis Guide)" was used on the website ftp://ftp.meta.moleculardevices.com/pub/uic/software/MX31R13/HelpDocs/MetaXpress/MetaXpress_3_1_Analysis_Guide.pdf) to design an analysis module. An automatic analysis was performed according to the following optimal indicators (a)~(c) for image analysis with 32 steps.

(a) Definition of Neurons

The cultured cells including neurons and glial cells were firstly separated according to the area and the fluorescence intensity of the nucleus stained by Hoechst dye together with MAP2 antibody. For example, built-in options of the MetaXpress 3.1 were used to set up 16 steps according to the following orders:

1: Configure Count Nuclei Data Log( )
2: Configure Count Nuclei Summary Log( )
3: Overwrite "Nuclear_All"=Count Nuclei (Src="DAPI")
4: Threshold Image([3: Count Nuclei], 1, 65535, Inclusive)
5: Create Regions Around Objects ([3: Count Nuclei])
6: Transfer Regions([3: Count Nuclei], "DAPI", ALLREGIONS and CLEARSOURCE and CLEARDEST)
7: Preferences( )
8: Threshold Image["DAPI", 1, 65535, Inclusive]
9: Integrated Morphometry—Load State("NeuriteNuclear test")
10: Integrated Morphometry—Measure("DAPI")
11: Integrated Morphometry—Create Objects Mask( )
12: Untitled=New(1392, 1040, 16, 0)
13: Overwrite "Nuclear_IMA"=[12: New]+"IMA Objects Mask"
14: Configure Neurite Outgrowth Data Log( )
15: Configure Neurite Outgrowth Summary Log( )
16: [None]=Neurite Outgrowth(NeuriteSrc="FITC", NuclearSrc=[13:Arithmetic], NuclearDest=Overwrite"Nuclear_Neurite")

All the nuclei in the image were counted according to the area and the fluorescence intensity. The nuclei overlapped with neuronal marker MAP2 were also selected so as to acquire neurons.

(b) Analysis of Neurite Outgrowth

After neurons stained with MAP2 were selected, the area of neuronal cell body, the length and the number of processes and branches of the neurites were calculated to verify outgrowth of the neurites. For example, built-in options of the MetaXpress 3.1 were used to set up 6 steps according to the following orders:

17: Threshold Image([16: Neurite Outgrowth], 1, 65535, Inclusive)
18: Overwrite "NeuriteNuclear_Binary"=Clip Image(16, [16: Neurite Outgrowth])
19: Overwrite "Add"="FITC"+[18: Clip Image]
20: Configure Neurite Outgrowth Data Log( )
21: Configure Neurite Outgrowth Summary Log( )
22: Overwrite "Neurite": Neurite Outgrowth(NeuriteSrc=[19: Arithmetic], NuclearSrc==[None], NuclearDest=[None])

Thereby the area of neuronal cell body, the length and the number of processes and branches of the neurites extended from the neurons were analyzed.

(c) Analysis of Synaptic Puncta Outgrowth of Neurons

Numbers of synaptic puncta of the neurons were calculated according to the area of the neurites labeled with fluorescence mentioned above to verify formation of the synaptic puncta of the neurons. For example, built-in options of the MetaXpress 3.1 were used to set up 10 steps according to the following orders:

23: Configure Cell Scoring Data Log( )
24: Configure Cell Scoring Summary Log( )
25: Overwrite "NeuronBinary"=Cell Scoring(All nuclei=[18: Clip Image], Positive marker="FITC")
26: Threshold Image([25: Cell Scoring], 1, 65535, Inclusive)
27: Overwrite "Binary"=Binarize([25: Cell Scoring]), 1, 65535
28: Overwrite "AND"="Cy5" AND [27: Binary Operations]
29: Configure Transfluor Data Log( )
30: Configure Transfluor Summary Log( )
31:[None]=Transfluor(Pit/Vesicle Source=[28: Arithmetic], Nuclear Source=[18:Clip Image])
32: Close All(NOQUERY)

Thereby the neuronal cell body and the area labeled with MAP2 were counted to get numbers of synaptic puncta within the area of the neurons.

The outgrowth of nerves and formation of neural network were learned by the above 32 steps. For example, 591 images in 197 fields of view labeled with three fluorescences at one well were analyzed by this module and it took only 2 hours to get the analysis result.

Figure 3:
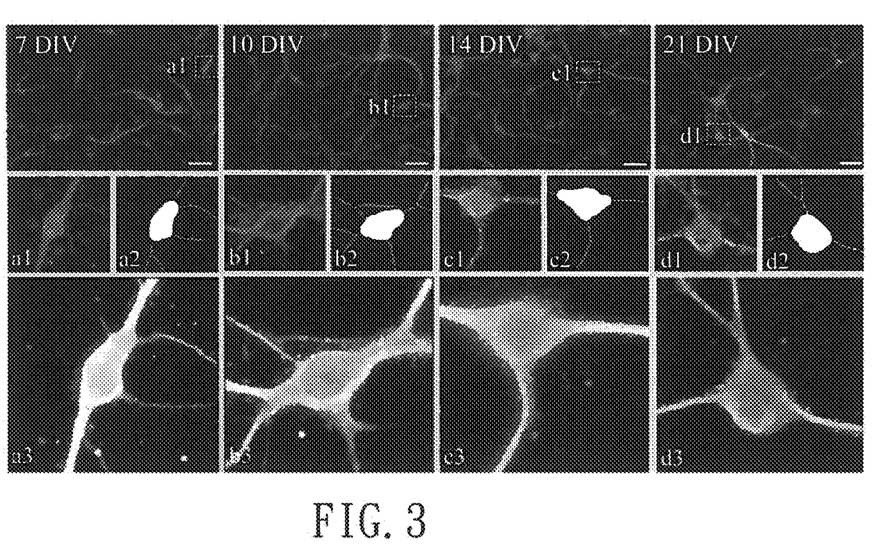
FIG. 3 shows images of neuron at different culture days according to the present invention.

Refer to FIG. 3, the cortical neurons were cultured for 7, 10, 14, and 21 days in vitro (DIV), and then were stained with neuronal cell body and dendrites (anti-MAP2, green), pre-synaptic puncta (anti-synaptophysin, red), and nucleus (Hoechst, blue). The scale bar in the figure is 50 nm.

Figure 4:
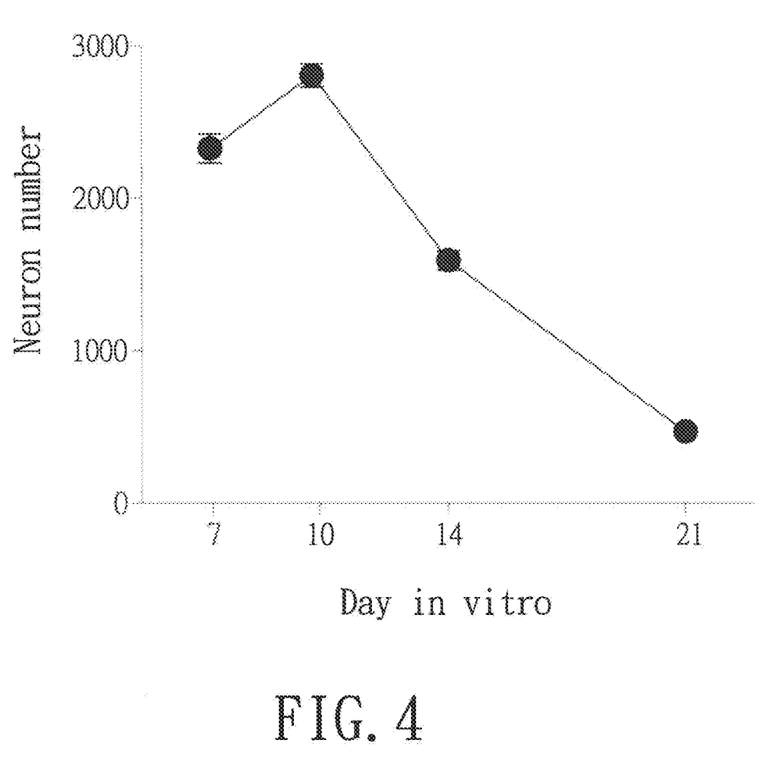
FIG. 4 is a schematic drawing showing the effect of culture days on the neuron number according to the present invention.
Figure 5:
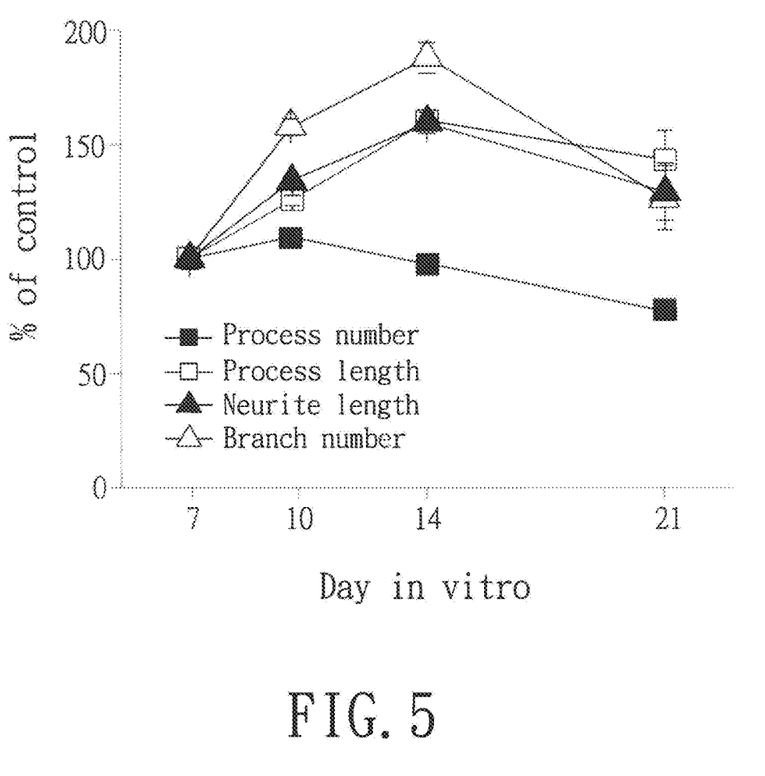
FIG. 5 is a schematic drawing showing the effect of culture days on neurite outgrowth according to the present invention.
Figure 6:
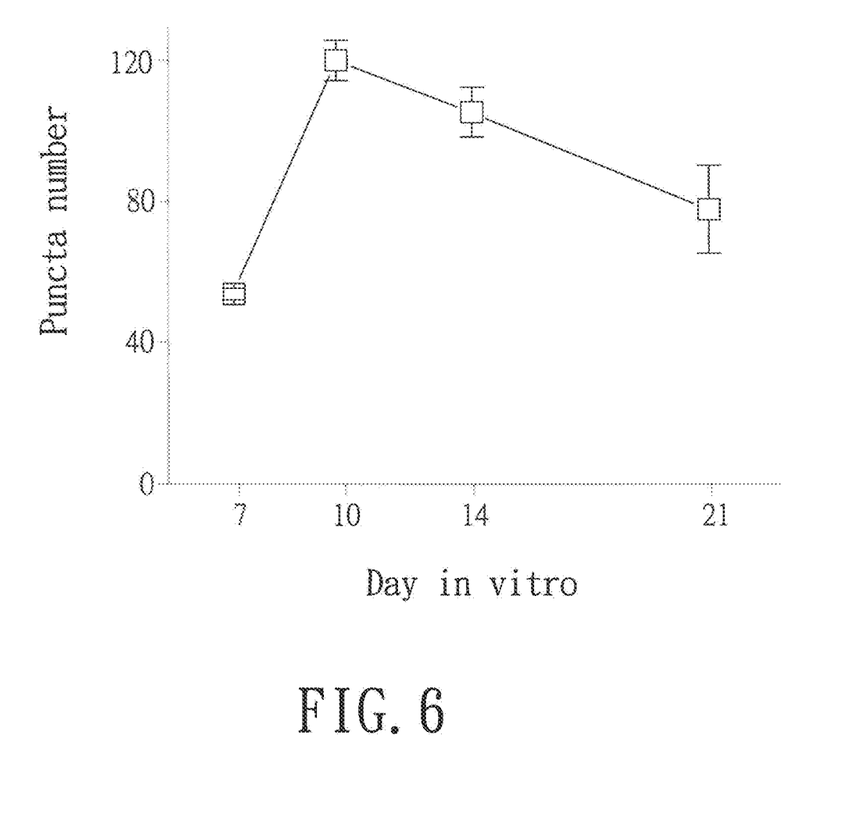
FIG. 6 is a schematic drawing showing the effect of culture days on (synaptic) puncta number according to the present invention.

After being analyzed according to the above 32 steps, test results of the primarily cultured cells as shown in FIG. 4, FIG. 5 and FIG. 6 were acquired. Referring to FIG. 4, the number of normal neurons counted was highest at the tenth day. Referring to FIG. 5, the process length, the neurite length and the branch number were best at the fourteenth day. Referring to FIG. 6, numbers of synaptic puncta reached the plateau at the tenth day and decreased at the fourteenth day. Therefore, 10 days in vitro is the optimal point for assessing neuronal function comprehensively in this image-based screening system.

Embodiment Three

Detecting the Effect of Chemotherapy Drugs on Neurons (1) Preparation of Primarily Cultured Cell Cerebral cortex was obtained from 0~1 day old B6 mice pup and meninges were removed. DMEM/F12 medium without serum was used to triturate the cortex tissue. Then, the DMEM/F12 medium without serum was refilled to 5 mL, mixed evenly with 0.5 mL trypsin, and placed at 37° C. for 5 minutes. Then the mixture with 1 mL FBS was filtered through a cell strainer. After a centrifugation at 3,000 rpm for 10 min, the supernatant was removed and precipitated cells were added to a medium required for nerve cell culture. The medium was prepared by adding B-27® Supplement, 0.5 mM L-glutamine, and 0.5% penicillin streptomycin to Neurobasal® A medium.

(2) Black multi-well microplates with clear bottom were used for nerve cell culture. Each well was coated with 70 μL poly-D-lysine or poly-L-lysine. Cells were seeded in a density of $2.8 \times 10^4$/well. After cells were cultured for 10 days, chemotherapy drugs listed in the table 1 was respectively added to react with cells for 24 hours. Then cells were fixed with 4% polyformaldehyde for 10 min and washed with PBS twice for 5 min each. Then, each well was added with 1 M glycine reacting for 10 min and wash with PBS twice for 5 min each. After cells were added with 0.05% Triton X-100 reacting for 20 min and washed with PBS twice for 5 min each, cell were blocked with 4% BSA for 1 hour and then stained with primary antibodies including anti-MAP2 antibody (MyBioSource; MBS502140) and anti-synaptophysin antibody (Abcam; ab32127) for 12-16 hours. Next, cells were washed twice with PBST (10 min each) and incubated with fluorescence-conjugated secondary antibodies including Alexa Fluor 488 (Jackson ImmunoResearch; 703-546-155) and Alexa Fluor 647 (molecular probes; A31573) and Hoechst 33258 for 1 hour. At last, cells were washed twice with PBST (10 min each) and added with PBS for further image acquisition and analysis.

TABLE 1

| Chemotherapy drugs | Concentration (nM) |
|---|---|
| Cisplatin | $10^2$~$10^4$ |
| Carboplatin | $10^3$~$10^5$ |
| Paclitaxel | $10^2$~$10^4$ |
| Vincristine | $10^0$~$10^2$ |
| Doxorubicin | $10^0$~$10^2$ |
| Lipo-Dox ® | $10^0$~$10^2$ |
| Topotecan | $10^0$~$10^1$ |
| Gemcitabine | $10^3$~$10^5$ |

(3) Fluorescence microscopy system and method mentioned in the above embodiment were used to capture images at the wavelength of DAPI, FITC, and Cy5 for image analysis of the cultured cells. The images were enlarged 200 times (200×) and saved automatically after the shooting for analysis.

Figure 7:
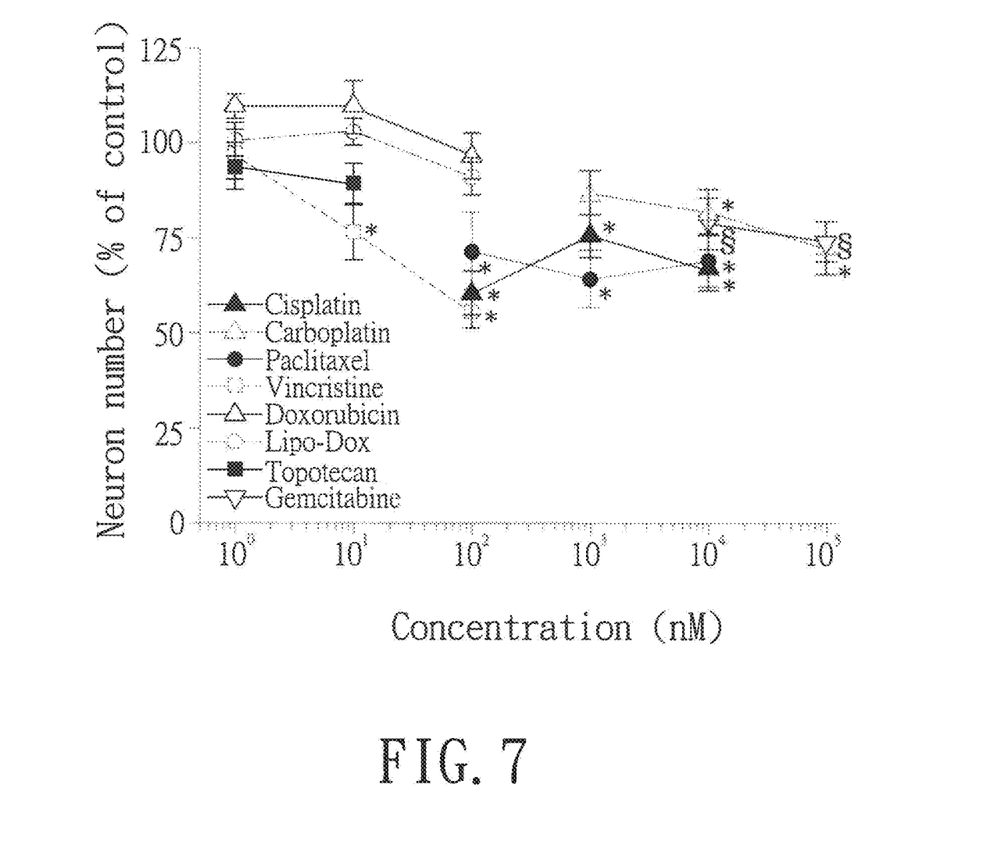
FIG. 7 is a schematic drawing showing effect of different chemotherapy drugs on the neuron number according to the present invention.
Figure 8:
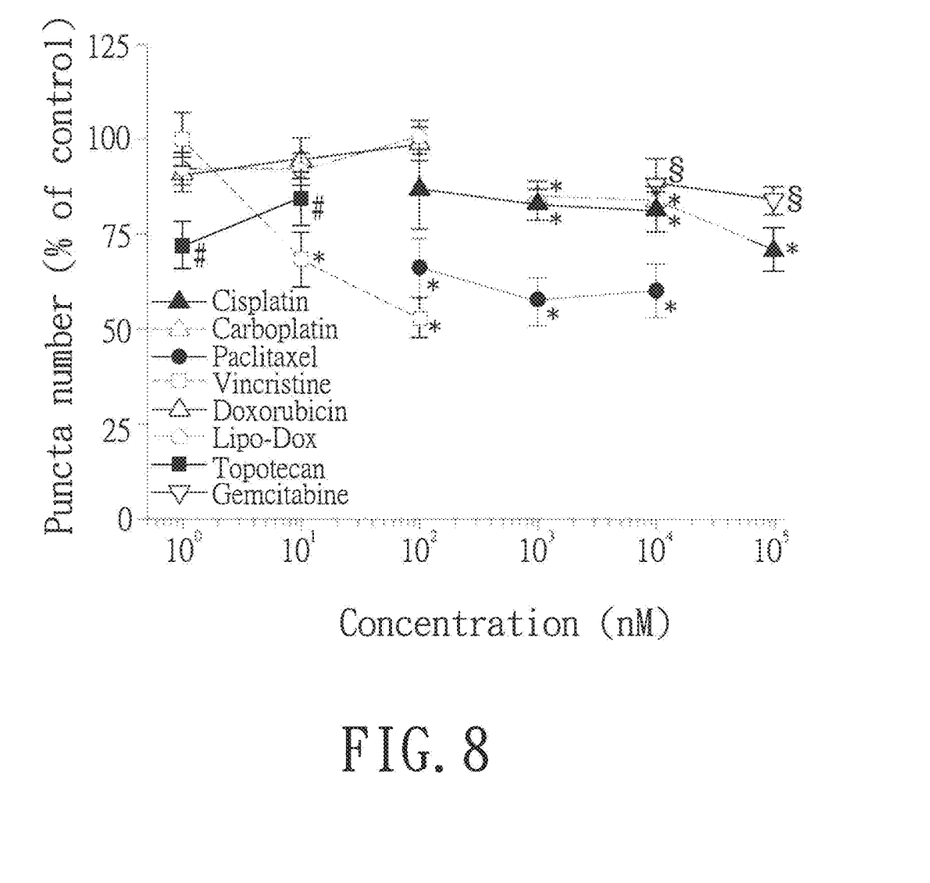
FIG. 8 is a schematic drawing showing effect of different chemotherapy drugs on (synaptic) puncta number according to the present invention.
Figure 9:
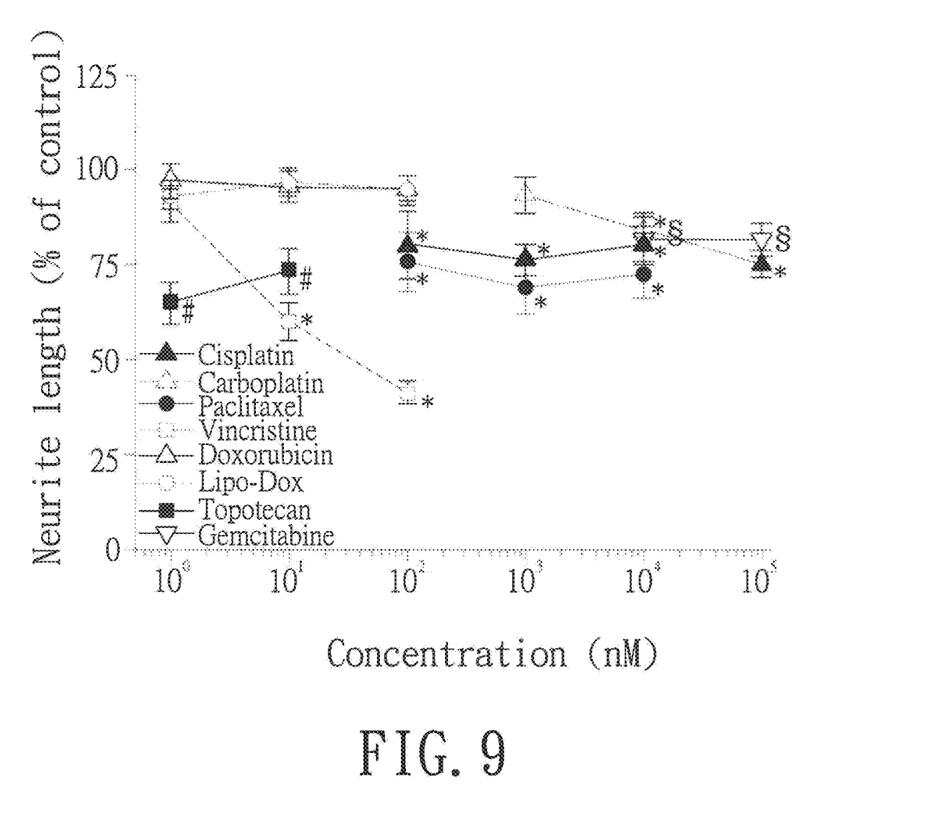
FIG. 9 is a schematic drawing showing effect of different chemotherapy drugs on neurite length according to the present invention.

Referring to FIG. 7, FIG. 8, and FIG. 9, the effect of different chemotherapy drugs on the neuron number, the synaptic puncta number and the neurite length was revealed. The results showed that vincristine and paclitaxel induced severe neurotoxicity. Compared with cisplatin, carboplatin had less neurotoxicity. As to topoisomerase inhibitors including doxorubicin and Lipo-Dox®, and nucleoside analogue-Gemcitabine, all caused less neurotoxicity.

After cell culture and image acquisition, the optimized module of the present invention (32 steps) was used in combination with high-throughput screening for analysis of neural function. Various analysis results were obtained quickly. The method of the present invention can be not only applied to screen and test neuron-related drugs (such as neuroprotective or neurotoxic effect of the drug on the nerve system) but also used to study functions and mechanisms of the nerve system in the academic community.

In summary, the present invention has following advantages compared with techniques available now:

1. After repetitive tests, several representative indicators were selected and used for assessment of nerve growth and formation of neural network at early stage. Accordingly, the method of the present invention assesses neural functions accurately and efficiently.

2. The method of the present invention provided several important indicators and a module for assessment of neural function, while indicators without discrimination were excluded. Thus, the method solved problems of complication and time-consuming. Moreover, the method can be used as a drug screening platform for quick and comprehensive assessment of drug's neurotoxicity or protective effect on nerve system.

What is claimed is:

1. A method for identifying and assessing function of neurons in a co-culture, comprising:
   providing a co-culture containing neurons and non-neuronal cells;
   obtaining a first fluorescence signal identifying DNA of the neurons and the non-neuronal cells in the co-culture; a second fluorescence signal identifying neurites of the neurons in the co-culture; and a third fluorescence signal identifying synaptic puncta of the neurons in the co-culture;
   identifying the neurons in the co-culture by obtaining identity information including steps (a) to (c):
   (a) DNA of the neurons and the non-neuronal cells identified by a fluorescence intensity of the first fluorescence signal;
   (b) dimensions of an area containing the DNA of the neurons and the non-neuronal cells identified by an area of the first fluorescence signal; and
   (c) the DNA of the neurons and the non-neuronal cells, the dimensions of an area containing the DNA, and the neurites of the neurons identified by a merging comparison of steps (a) and (b);
   wherein the identified neurons are selected and the non-neuronal cells are excluded as noise by performance of steps (a) to (c);
   after identifying and selecting the neurons and excluding the non-neuronal cells, function of the identified neurons is assessed by:
   conducting a neuronal neurite outgrowth assessment by executing an outgrowth module on the identified and selected neurons using the second fluorescence signal and the identity information, wherein the outgrowth module measures outgrowth of an area of a neuron body, a length of a process, a number of process, branches of a neuron or a combination thereof; and
   conducting a synaptic puncta assessment by executing a cell scoring and transfluor module on the identified and selected neurons using the second fluorescence signal, the third fluorescence signal and the identity information, wherein the cell scoring and transfluor module measures outgrowth of synaptic puncta by a location of the synaptic puncta along with a length of a process,
   wherein performance of the outgrowth module and the cell scoring and transfluor module together provide assessment of the function of the identified neurons.

2. The method for identifying and assessing function of neurons in a co-culture of claim 1, wherein the first fluorescence signal is of Hoechst labeling.

3. The method for identifying and assessing function of neurons in a co-culture of claim 1, wherein the second fluorescence signal is of a fluorescence labeling to microtubule-associated protein 2 (MAP2), neuronal class III β-tubulin, or a combination thereof.

4. The method for identifying and assessing function of neurons in a co-culture of claim 3, wherein the second fluorescence signal is of a fluorescence labeling to microtubule-associated protein 2 (MAP2).

5. The method for identifying and assessing function of neurons in a co-culture of claim 1, wherein the third fluorescence signal is of a fluorescence labeling to synaptophysin, post synaptic density 95, or a combination thereof.

6. The method for identifying and assessing function of neurons in a co-culture of claim 5, wherein the third fluorescence signal is of a fluorescence labeling to synaptophysin.

7. The method for identifying and assessing function of neurons in a co-culture of claim 1, wherein the non-neuronal cell is astrocyte, microglia, or a combination thereof.

* * * * *